(12) United States Patent
Suzuki

(10) Patent No.: US 7,504,650 B2
(45) Date of Patent: Mar. 17, 2009

(54) APPARATUS FOR AND METHOD OF ERASING RESIDUAL RADIATION IMAGE

(75) Inventor: Kiyotaka Suzuki, Odawara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/494,512

(22) Filed: Jul. 28, 2006

(65) Prior Publication Data

US 2008/0023660 A1    Jan. 31, 2008

(30) Foreign Application Priority Data

Jul. 28, 2005    (JP)  ............................... 2005-218585

(51) Int. Cl.
G01N 23/02 (2006.01)
(52) U.S. Cl. .................................... 250/588
(58) Field of Classification Search ................ 250/580, 250/581, 582, 584, 588
See application file for complete search history.

(56) References Cited

U.S. PATENT DOCUMENTS

| | | | |
|---|---|---|---|
| 4,439,682 A | 3/1984 | Matsumoto et al. | |
| 4,786,808 A * | 11/1988 | Saito | ........................... 250/588 |
| 5,051,587 A | 9/1991 | Hara et al. | |
| 5,072,119 A * | 12/1991 | Yamaguchi | ................ 250/588 |
| 5,422,208 A | 6/1995 | Kojima et al. | |
| 5,434,431 A * | 7/1995 | Verbeke et al. | ............... 250/585 |
| 5,530,261 A * | 6/1996 | Yasuda | ........................ 250/588 |
| 6,339,225 B1 | 1/2002 | Funabashi | |
| 6,344,657 B1 | 2/2002 | Matsumoto et al. | |
| 7,196,345 B2 | 3/2007 | Shimada | |
| 7,250,622 B2 * | 7/2007 | Nakajo et al. | ................ 250/588 |
| 2002/0014606 A1* | 2/2002 | Yasuda | ........................ 250/587 |
| 2004/0089826 A1* | 5/2004 | Yonekawa | .................. 250/584 |
| 2004/0183039 A1* | 9/2004 | Iiyama | ........................ 250/589 |
| 2005/0156126 A1* | 7/2005 | Nakajo et al. | ................ 250/584 |
| 2005/0199837 A1* | 9/2005 | Shimada | ..................... 250/588 |
| 2005/0211932 A1* | 9/2005 | Kuwabara | ................... 250/584 |
| 2006/0145104 A1* | 7/2006 | Rogers et al. | ................ 250/588 |
| 2008/0023660 A1 | 1/2008 | Suzuki | |

FOREIGN PATENT DOCUMENTS

| JP | 5-119412 A | 5/1993 |
|---|---|---|
| JP | 6-175243 A | 6/1994 |

\* cited by examiner

*Primary Examiner*—David P Porta
*Assistant Examiner*—Marcus H Taningco
(74) *Attorney, Agent, or Firm*—Sughrue Mion, PLLC

(57) ABSTRACT

A stored quantity calculator calculates the quantity of radiation energy stored in each of divided areas of a stimulable phosphor panel. Erasing energy set to a level depending on the calculated quantity of radiation energy stored in each of the areas is applied from an erasing unit to the stimulable phosphor panel. Therefore, a residual radiation image remaining in the stimulable phosphor panel is efficiently erased with a required minimum level of erasing energy.

23 Claims, 8 Drawing Sheets

APPARATUS FOR AND METHOD OF ERASING RESIDUAL RADIATION IMAGE

BACKGROUND OF THE INVENTION

1. Field of the Invention

The present invention relates to an apparatus for and a method of erasing a residual radiation image from a stimulable phosphor panel by applying erasing light to the stimulable phosphor panel after a radiation image has been read from the stimulable phosphor panel by applying stimulating light to the stimulable phosphor panel.

2. Description of the Related Art

There has heretofore been known a stimulable phosphor which, when exposed to radiation (X-rays, α-rays, β-rays, γ-rays, electron beams, ultraviolet radiation, or the like), stores part of the energy of the radiation, and, when subsequently exposed to stimulating rays such as visible light, emits light in proportion to the stored energy of the radiation.

A radiation image information recording and reproducing system, which has been developed in the art, temporarily records a radiation image of a subject such as a human body on a stimulable phosphor panel having a stimulable phosphor layer. Thereafter, the radiation image information recording and reproducing system applies stimulating light such as a laser beam or the like to the stimulable phosphor panel to emit light representative of the recorded radiation image, and then outputs the radiation image as a visible image on a recording medium such as a photosensitive medium or the like or a display unit such as a CRT or the like, based on an image signal that is generated by photoelectrically reading the light emitted from the stimulable phosphor panel. After the radiation image has been read from the stimulable phosphor panel, the stimulable phosphor panel is irradiated with erasing light to erase any remaining radiation image therefrom, and then used again for recording a radiation image thereon.

If erasing light exclusive of ultraviolet radiation is used to erase the remaining radiation image from the stimulable phosphor panel, then electrons trapped in a deep layer where they cannot be removed by visible erasing light tend to remain unremoved. Conversely, if erasing light including much ultraviolet radiation is used, then though those trapped electrons can be removed from the deep layer, new trapped electrons are generated by the ultraviolet-rich erasing light itself.

In view of the above drawback, there has been developed a technology for efficiently erasing remaining radiation image information from a stimulable phosphor panel by applying first erasing light including a radiation in an ultraviolet wavelength range to the stimulable phosphor panel to remove trapped electrons from the deep layer region and thereafter applying second erasing light in a wavelength range other than the ultraviolet wavelength range to remove trapped electron that have newly been generated in a rather shallow layer by the first erasing light (see Japanese Laid-Open Patent Publication No. 5-119412).

The dose of radiation applied to the stimulable phosphor panel differs depending on the imaging conditions, the region of the subject that is to be imaged, etc. Therefore, the amount of remaining radiation energy differs depending on the position on the stimulable phosphor panel. Furthermore, stimulable phosphor panels for use in imaging subjects are available in various sizes depending on the purpose for which the image is captured.

If the level of erasing energy for erasing remaining radiation image information is established based on the maximum level of radiation energy that is stored in the stimulable phosphor panel and the remaining radiation image information is erased with the established level of erasing energy, then the remaining radiation image information can reliably be removed from the stimulable phosphor panel.

With such an erasing energy level setting, however, more erasing energy than necessary is applied to those areas of the stimulable phosphor panel where the maximum level of radiation energy is not stored. As a result, the erasing process tends to result in a wasteful consumption of electric energy. If the level of erasing energy is established based on the maximum stimulable phosphor panel size regardless of different stimulable phosphor panel sizes that are actually used, then some erasing energy is also wasted.

SUMMARY OF THE INVENTION

It is a general object of the present invention to provide an apparatus for and a method of efficiently and reliably erasing a residual radiation image from a stimulable phosphor panel with a required minimum level of erasing energy.

A principal object of the present invention is to provide an apparatus for and a method of efficiently erasing radiation energy remaining in a stimulable phosphor panel by applying erasing light having appropriate erasing energy depending on the residual radiation energy.

Another principal object of the present invention is to provide an apparatus for and a method of efficiently erasing a residual radiation image from a stimulable phosphor panel by applying erasing light to an area of the stimulable phosphor panel which depends on the size of the stimulable phosphor panel.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
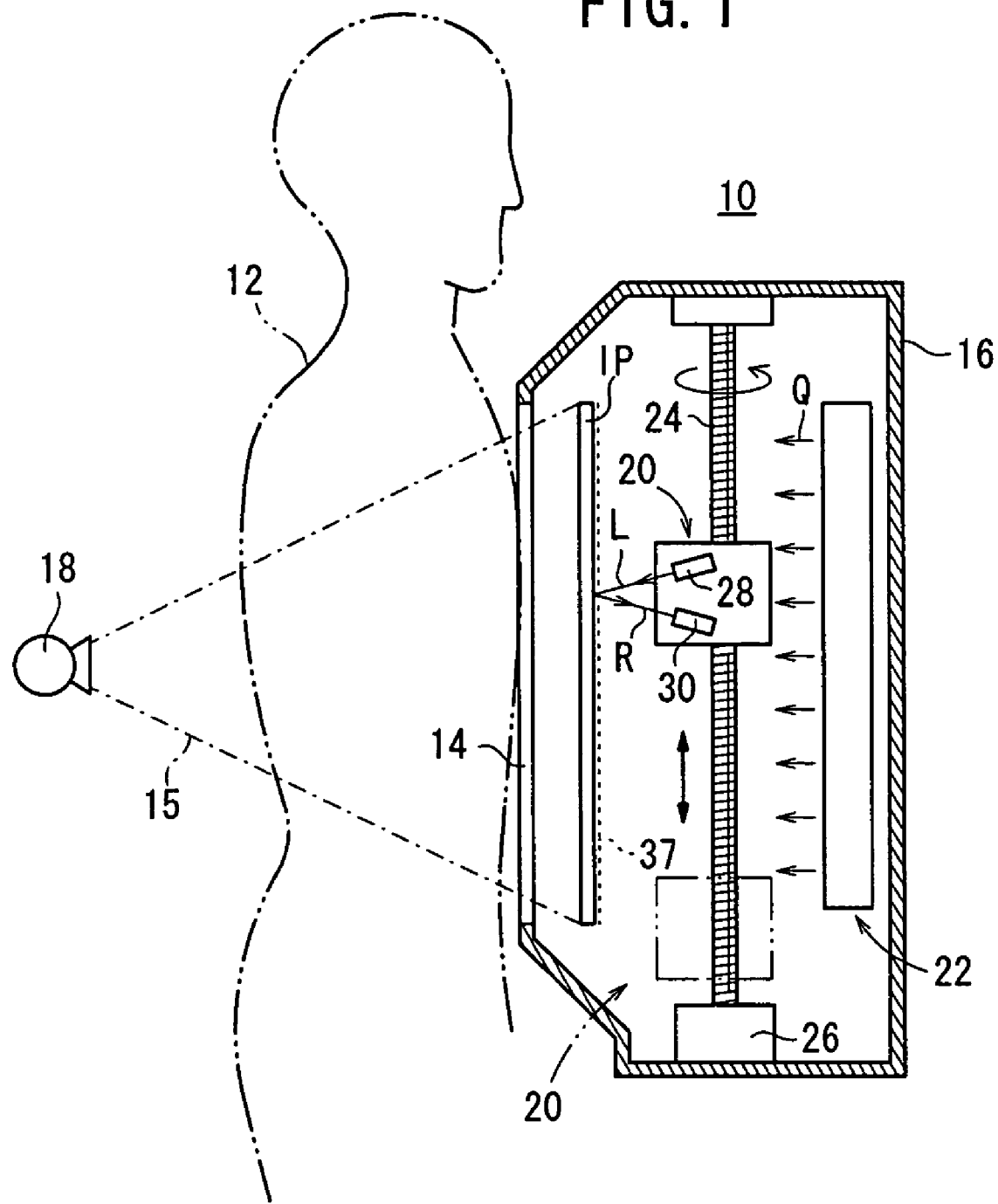
FIG. 1 is a vertical cross-sectional view of an upright imaging system incorporating therein an apparatus for and a method of erasing a residual radiation image according to the present invention.

FIG. 1 shows in vertical cross section an upright imaging system 10 incorporating therein an apparatus for and a method of erasing a residual radiation image according to the present invention.

As shown in FIG. 1, the upright imaging system 10 has, in addition to a function to record a radiation image of a subject 12 such as a human body or the like on a stimulable phosphor panel IP, a function to read a radiation image from a stimulable phosphor panel IP, and a function to erase a residual radiation image which remains in a stimulable phosphor panel IP from which a recorded radiation image has been read.

The stimulable phosphor panel IP may comprise a hard panel having a columnar stimulable phosphor layer vapor-deposited on a support board of a hard material such as glass or the like. The columnar stimulable phosphor layer may be formed by any of various processes including a vacuum evaporation process in which a stimulable phosphor is heated and evaporated in a vacuum container and then deposited on the support board, a sputtering process, a CVD process, and an ion plating process. The columnar stimulable phosphor layer has the stimulable phosphor formed as optically independent columns substantially perpendicular to the plane of the stimulable phosphor panel IP. The columns of the columnar stimulable phosphor are highly sensitive to a radiation applied thereto, lower the granularity of images recorded therein, and reduce the scattering of stimulating light applied thereto for producing sharp images.

However, the stimulable phosphor panel IP is not limited to the structure wherein a columnar stimulable phosphor layer is formed on a support board of a hard material. The stimulable phosphor panel IP may comprise a sheet wherein a flexible support board is coated with a stimulable phosphor. In the upright imaging system 10 according to the present embodiment, the stimulable phosphor panel IP is of the type wherein a stimulable phosphor layer is formed on a transparent support board for recording a radiation image from one surface and reading a recorded radiation image and erasing a residual radiation image from the other surface. Dependent on the structural details of the upright imaging system 10, the stimulable phosphor panel IP may be of the type wherein a radiation image is recorded, read, and erased from one surface.

The upright imaging system 10 comprises a vertical imaging base 14 for positioning a region to be imaged of the subject 12, and a casing 16 coupled to the imaging base 14 and providing, together with the imaging base 14, a light-shielded chamber in the upright imaging system 10. An X-ray source 18 is disposed in facing relation to the imaging base 14 for applying an X-ray radiation 15 to the subject 12.

The stimulable phosphor panel IP is disposed in the casing 16 of the upright imaging system 10 substantially parallel to the imaging base 14. The casing 16 houses therein a reading unit 20 for reading a radiation image recorded in the stimulable phosphor panel IP and an erasing unit 22 for erasing a residual radiation image from the stimulable phosphor panel IP after the radiation image has been read from the stimulable phosphor panel IP.

The reading unit 20 is threaded over a ball screw 24 extending vertically in the casing 16. When the ball screw 24 is rotated about its own axis by a motor 26 coupled to the lower end of the ball screw 24, the reading unit 20 is vertically moved on and along the ball screw 24. The reading unit 20 comprises a stimulating light source 28 for applying stimulating light L to the stimulable phosphor panel IP on which a radiation image has been recorded, and a photoelectric transducer 30 for detecting stimulated light R representing the radiation image which is emitted from the stimulable phosphor panel IP when it is irradiated with the stimulating light L, and converting the stimulated light R into an electric signal.

The stimulating light source 28 may comprise a linear array of light-emitting diodes extending along the main scanning direction, i.e., a direction normal to the sheet of FIG. 1, of the stimulable phosphor panel IP. The photoelectric transducer 30 may comprise a CCD line sensor for detecting the stimulated light R emitted from the stimulable phosphor panel IP when the stimulating light L from the stimulating light source 28 is applied to the stimulable phosphor panel IP while scanning the stimulable phosphor panel IP in the main scanning direction. At this time, the reading unit 20 may be moved in the auxiliary scanning direction indicated by the arrow along the ball screw 24, i.e., the stimulable phosphor panel IP, so that the radiation image recorded in the stimulable phosphor panel IP can be read two-dimensionally.

Figure 2:
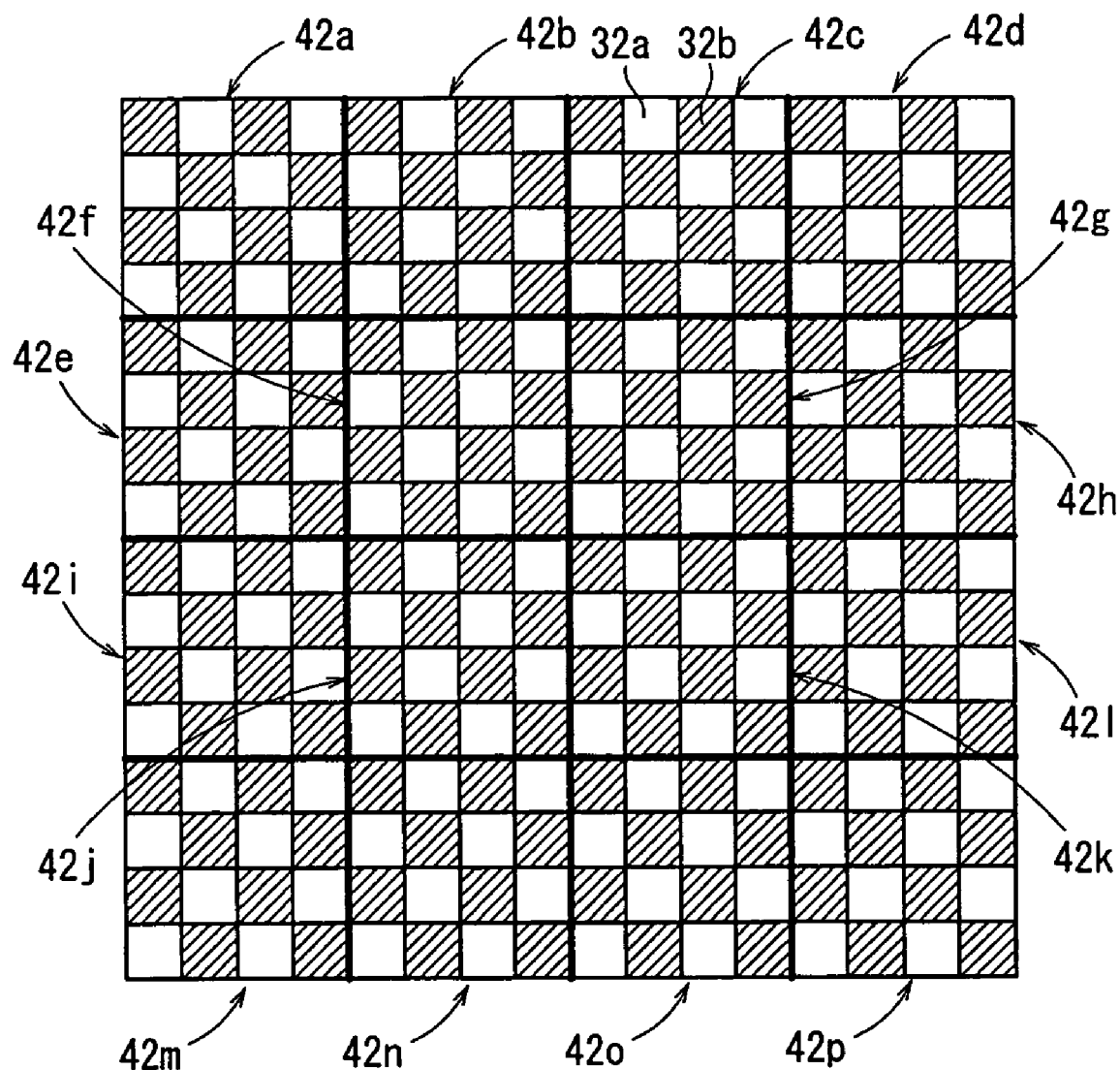
FIG. 2 is a view of erasing light sources of an erasing unit in the upright imaging system shown in FIG. 1.

The erasing unit 22 is disposed in confronting relation to the stimulable phosphor panel IP across the reading unit 20. As shown in FIG. 2, the erasing unit 22 comprises a number of erasing light sources 32a, 32b, each for emitting erasing light Q, alternately arranged in a two-dimensional matrix.

Each of the erasing light sources 32a (first erasing elements) emits first erasing light Q1 including a radiation in a wavelength range shorter than 500 nm, and each of the erasing light sources 32b (second erasing elements) emits second erasing light Q2 comprising only a radiation in a wavelength range equal to or longer than 500 nm. These erasing light sources 32a, 32b may comprise light-emitting elements such as light-emitting diodes or the like. If the erasing light sources 32a, 32b comprise light-emitting elements, then the erasing unit 22 is of a thin structure. Alternatively, each of the erasing light sources 32a, 32b may emit erasing light Q including a radiation in a short wavelength range and a radiation in a long wavelength range, with a filter being disposed in front of each of the erasing light sources 32b for filtering out the radiation in the short wavelength range.

The erasing unit 22 has its entire erasing light emitting area divided into a plurality of erasing blocks 42a through 42p. Each of the erasing blocks 42a through 42p includes a plurality of erasing light sources 32a, 32b.

Figure 3:
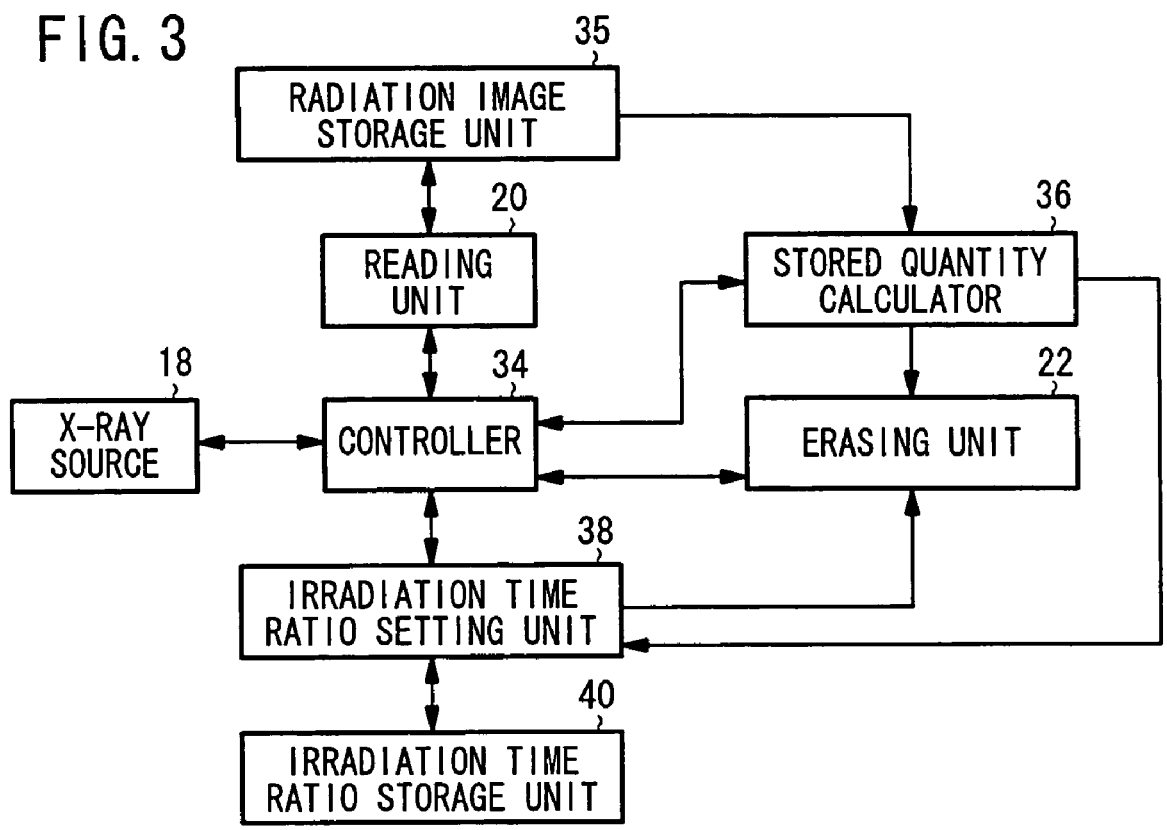
FIG. 3 is a block diagram of a control circuit in the upright imaging system shown in FIG. 1.

FIG. 3 shows in block form a control circuit of the upright imaging system 10.

As shown in FIG. 3, the upright imaging system 10 is controlled by a controller 34. Specifically, the controller 34 controls the X-ray source 18 according to the imaging conditions, and also controls the reading unit 20 and the erasing unit 22. A radiation image that has been read from the stimulable phosphor panel IP by the reading unit 20 is stored in a radiation image storage unit 35.

A stored quantity calculator 36 divides the radiation image stored in the radiation image storage unit 35 into a plurality of areas corresponding respectively to the erasing blocks 42a through 42p of the erasing unit 22, and calculates the quantity of radiation energy stored in the stimulable phosphor panel IP with respect to each of the divided areas based on the maximum value of the radiation image in each of the divided areas thereof. The radiation image storage unit 35 and the stored quantity calculator 36 jointly make up a stored quantity detecting means.

Instead of calculating the quantity of stored radiation energy from the radiation image, a phototimer 37 (radiation dose detector) for detecting the dose of the X-ray radiation 15 that has passed through the stimulable phosphor panel IP may be disposed along the stimulable phosphor panel IP, as shown in FIG. 1, and the quantity of radiation energy stored in the stimulable phosphor panel IP with respect to each of the divided areas may be calculated from the dose detected in each of the divided areas by the phototimer 37.

The phototimer 37 detects the dose of the X-ray radiation 15 that has passed through the subject 12 and the stimulable phosphor panel IP. If the detected dose exceeds a predetermined upper limit dose set depending on the subject region to be imaged, the imaging conditions, etc., then the phototimer 37 forcibly stops supplying a high voltage to the X-ray source 18, thereby preventing in advance the subject 12 from being excessively exposed to the X-ray radiation 15. The phototimer 37 is made of a material permeable to the stimulating light L and the stimulated light R so as not to interfere with the reading of the radiation image by the reading unit 20.

The quantity of radiation energy calculated for each of the divided areas by the stored quantity calculator 36 is supplied to an irradiation time ratio setting unit 38. The irradiation time ratio setting unit 38 reads an optimum irradiation time ratio for the first erasing light Q1 and the second erasing light Q2 with respect to the calculated quantity of stored radiation energy, from an irradiation time ratio storage unit 40 (irradiation time ratio storing means), and supplies the read optimum irradiation time ratio to the erasing unit 22.

The irradiation time ratio storage unit 40 stores beforehand optimum irradiation time ratios for the first erasing light Q1 and the second erasing light Q2 with respect to the quantities of radiation energy that may be stored in the stimulable phosphor panel IP.

Figure 4:
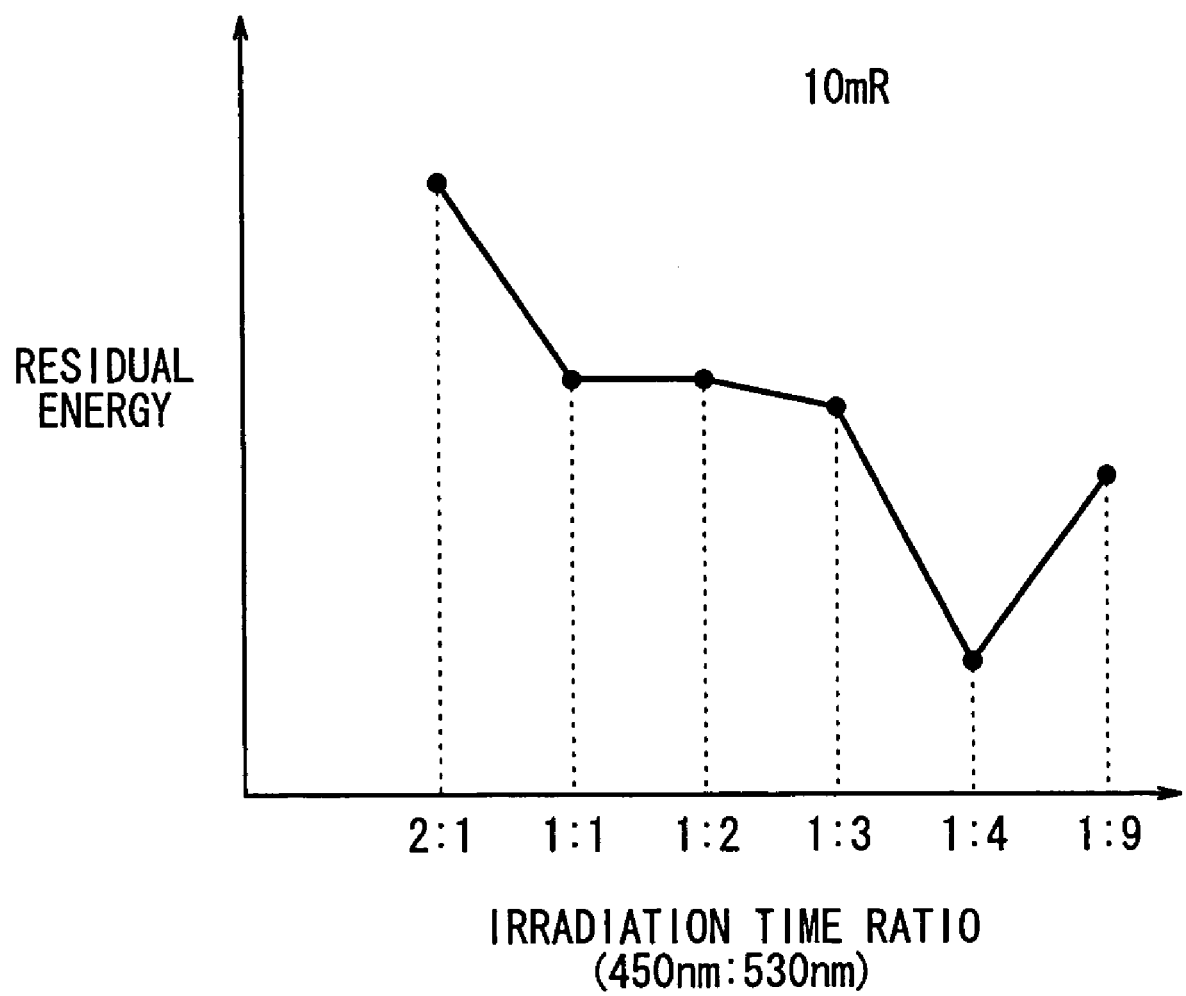
FIG. 4 is a diagram showing the relation between irradiation time ratios and amounts of remaining energy at the time the dose of radiation energy is 10 mR.
Figure 5:
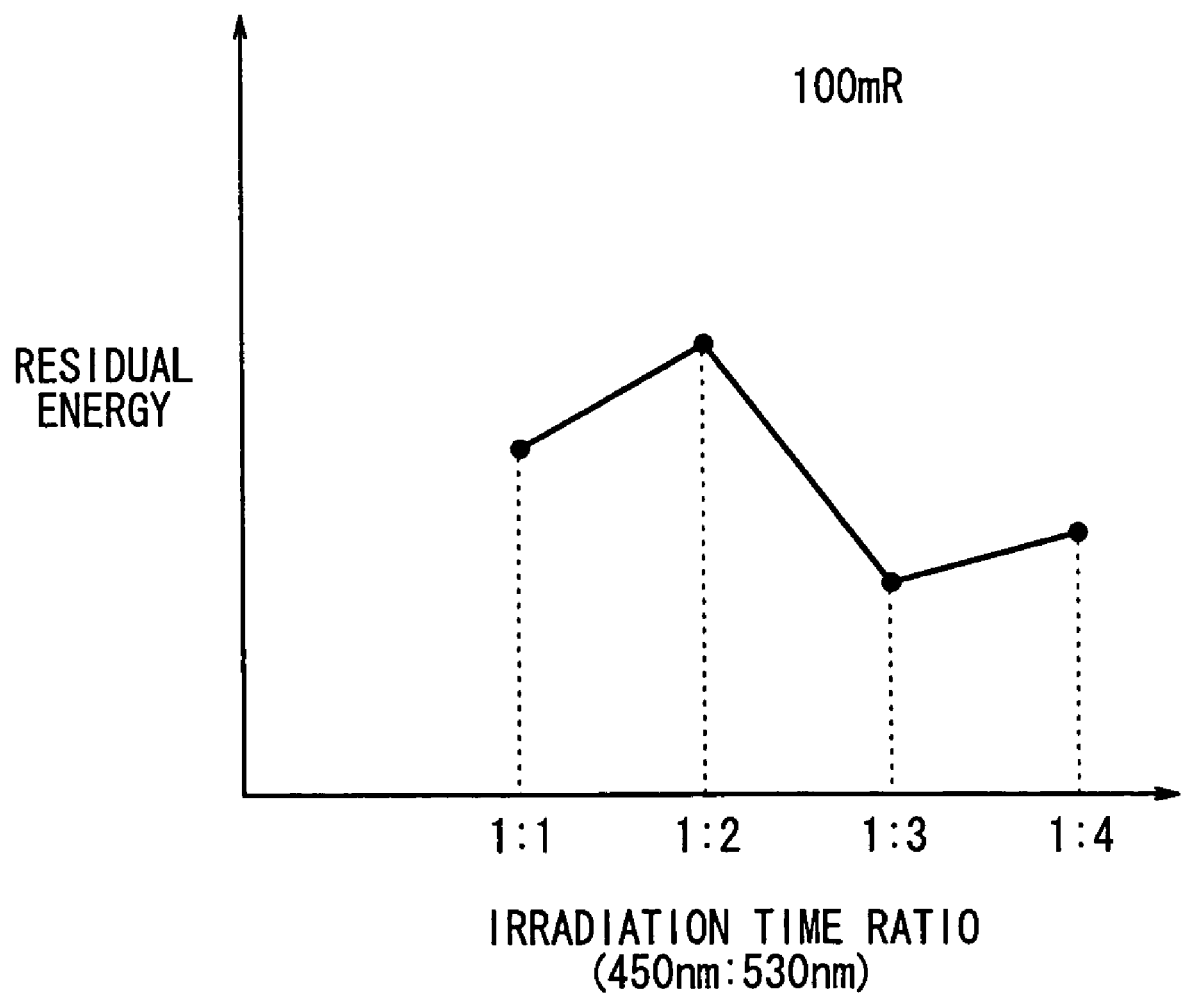
FIG. 5 is a diagram showing the relation between irradiation time ratios and amounts of remaining energy at the time the dose of radiation energy is 100 mR.
Figure 6:
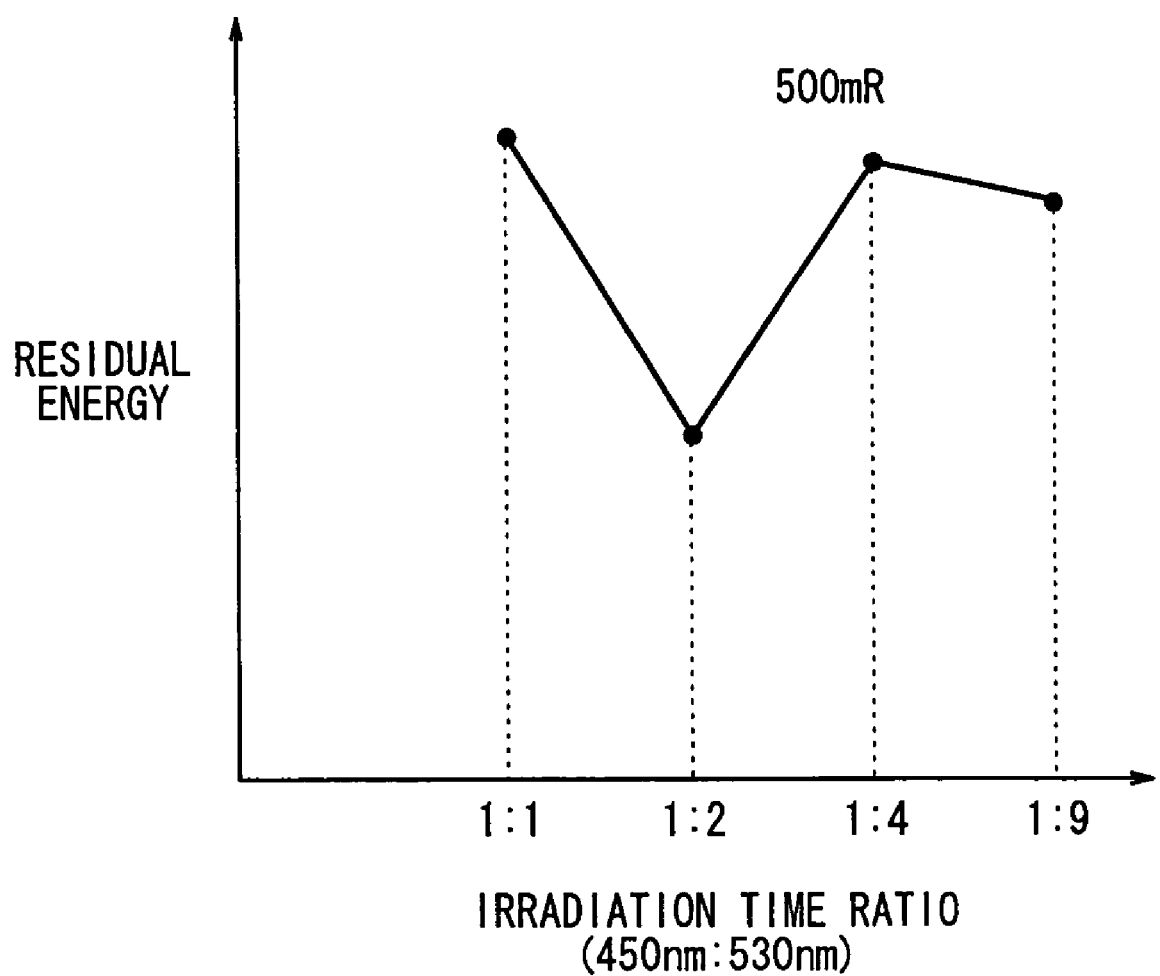
FIG. 6 is a diagram showing the relation between irradiation time ratios and amounts of remaining energy at the time the dose of radiation energy is 500 mR.

FUJI PHOTO FILM CO., LTD. combined doses of the X-ray radiation 15 applied to the stimulable phosphor panel IP and irradiation time ratios of the first erasing light Q1 having a wavelength of 450 nm and the second erasing light Q2 having a wavelength of 530 nm in various combinations, applied the first erasing light Q1 and the second erasing light Q2 at a given irradiation energy level to the stimulable phosphor panel IP for 90 seconds, and thereafter measured amounts of energy remaining in the stimulable phosphor panel IP. The measured values are shown in FIGS. 4 through 6. FIG. 4 illustrates measured results obtained when the dose of the X-ray radiation 15 was 10 mR ($\approx 2.58 \times 10^{-6}$ C/kg), FIG. 5 measured results obtained when the dose of the X-ray radiation 15 was 100 mR ($\approx 2.58 \times 10^{-5}$ C/kg), and FIG. 6 measured results obtained when the dose of the X-ray radiation 15 was 500 mR ($\approx 1.29 \times 10^{-4}$ C/kg).

It can be seen from the illustrated measured results that when the dose of the X-ray radiation 15 is low (see FIG. 4), if the irradiation time ratio of the first erasing light Q1 to the second erasing light Q2 is smaller, the amount of energy remaining in the stimulable phosphor panel IP is reduced, indicating that the remaining radiation image can efficiently be erased. It can also be understood that when the dose of the X-ray radiation 15 is high (see FIG. 6), if the irradiation time ratio of the first erasing light Q1 to the second erasing light Q2 is greater than that when the dose of the X-ray radiation 15 is low, the amount of energy remaining in the stimulable phosphor panel IP is reduced, indicating that the remaining radiation image can efficiently be erased.

The reasons for the above measured results are that when the dose of the X-ray radiation 15 is low, trapped electrons distributed in a deep layer of the stimulable phosphor panel IP are reduced, and much of the first erasing light Q1 including the high-energy radiation in the short wavelength range is not required, but primarily the second erasing light Q2 including the radiation in the long wavelength range is applied to the stimulable phosphor panel IP, thereby sufficiently removing the trapped electrons. On the other hand, when the dose of the X-ray radiation 15 is high, trapped electrons distributed in a deep layer of the stimulable phosphor panel IP are increased, and the first erasing light Q1 including the high-energy radiation in the short wavelength range is applied to the stimulable phosphor panel IP for a relatively long period of time to remove the trapped electrons in the deep layer. Thereafter, the second erasing light Q2 including the radiation in the long wavelength range is applied to the stimulable phosphor panel IP, thereby sufficiently removing the trapped electrons.

Based on the above measured results, the irradiation time ratio storage unit 40 stores irradiation time ratios for the first erasing light Q1 and the second erasing light Q2, which are capable of minimizing the residual radiation energy, with respect to the quantities of radiation energy that are stored in the stimulable phosphor panel IP depending on the dose of the X-ray radiation 15 applied to the stimulable phosphor panel IP.

The upright imaging system 10 according to the present embodiment is basically constructed as described above. Operation and advantages of the upright imaging system 10 will be described below.

It is assumed that the stimulable phosphor panel IP from which any residual radiation image has completely been erased is set in the upright imaging system 10. After the subject 12 is positioned in a given area on the imaging base 14, the X-ray source 18 is controlled according to the subject region to be imaged, the imaging conditions, etc. to apply the X-ray radiation 15 to the subject 12. Part of the X-ray radiation 15 applied to the subject 12 passes through the subject 12 and is applied to the stimulable phosphor panel IP, recording a radiation image of the subject 12 in the stimulable phosphor panel IP.

After the radiation image is recorded in the stimulable phosphor panel IP, the reading unit 20 is energized to start reading the radiation image from the stimulable phosphor panel IP. Specifically, the motor 26 is energized to rotate the ball screw 24 about its own axis, moving the reading unit 20 in the auxiliary scanning direction indicated by the arrow along the stimulable phosphor panel IP. At this time, the stimulating light L emitted from the stimulating light source 28 is applied as a line of light in the main scanning direction to the stimulable phosphor panel IP. Upon exposure to the stimulating light L, the stimulable phosphor panel IP emits stimulated light R which depends on the recorded radiation image. The stimulated light R emitted from the stimulable phosphor panel IP is converted by the photoelectric transducer 30 into an electric signal, which is stored as representing the radiation image in the radiation image storage unit 35. In this manner, the radiation image recorded in the stimulable phosphor panel IP is two-dimensionally read from the stimulable phosphor panel IP.

After the reading unit 20 has read the radiation image recorded in the stimulable phosphor panel IP, the erasing unit 22 is energized to start erasing a residual radiation image in the stimulable phosphor panel IP. The stored quantity calculator 36 reads the radiation image stored in the radiation image storage unit 35, and calculates the maximum level of radiation energy stored in the stimulable phosphor panel IP with respect to each of the divided areas corresponding to the respective erasing blocks 42a through 42p of the erasing unit 22. The calculated maximum level of stored radiation energy with respect to each of the divided areas is supplied to the erasing unit 22 and the irradiation time ratio setting unit 38. The irradiation time ratio setting unit 38 reads the irradiation time ratio for the first erasing light Q1 and the second erasing light Q2 which corresponds to the maximum level of stored radiation energy with respect to each of the divided areas, from the irradiation time ratio storage unit 40, and supplies the read irradiation time ratio to the erasing unit 22.

Based on the maximum level of stored radiation energy with respect to each of the divided areas supplied from the stored quantity calculator 36, the erasing unit 22 calculates an amount of erasing energy that is required to erase residual radiation energy with each of the erasing blocks 42a through 42p. Then, the erasing unit 22 energizes the erasing light sources 32a, 32b of the erasing blocks 42a through 42p for an irradiation time in which the erasing light sources 32a, 32b can apply the calculated amount of erasing energy at the irradiation time ratio supplied from the irradiation time ratio setting unit 38, thereby erasing the residual radiation image from the stimulable phosphor panel IP.

Specifically, based on the irradiation time ratio, the erasing light sources 32a are energized to apply only the first erasing light Q1 including the radiation in the short wavelength range for the irradiation time to the stimulable phosphor panel IP. Thereafter, the erasing light sources 32b are energized to apply only the second erasing light Q2 including the radiation in the long wavelength range for the irradiation time to the stimulable phosphor panel IP. Trapped electrons remaining in the deep layer of the stimulable phosphor panel IP are reliably removed by the first erasing light Q1, and then trapped electrons remaining in the relatively shallow layer of the stimulable phosphor panel IP are reliably removed by the second erasing light Q2.

As described above, an appropriate amount of erasing energy is applied to the stimulable phosphor panel IP with respect to each of the divided areas of the radiation image stored therein, so that the residual radiation image in the stimulable phosphor panel IP can reliably be removed therefrom. As no significant radiation image remains in the stimulable phosphor panel IP after it has been processed by the erasing unit 22, a new radiation image can be recorded highly accurately in the stimulable phosphor panel IP without being adversely affected by any residual radiation image. The erasing blocks 42a through 42p for emitting the erasing light Q may selectively be inactivated depending on the size of the stimulable phosphor panel IP that is used, for efficiently erasing residual radiation image from the stimulable phosphor panel IP without a wasteful consumption of electric energy.

Figure 7:
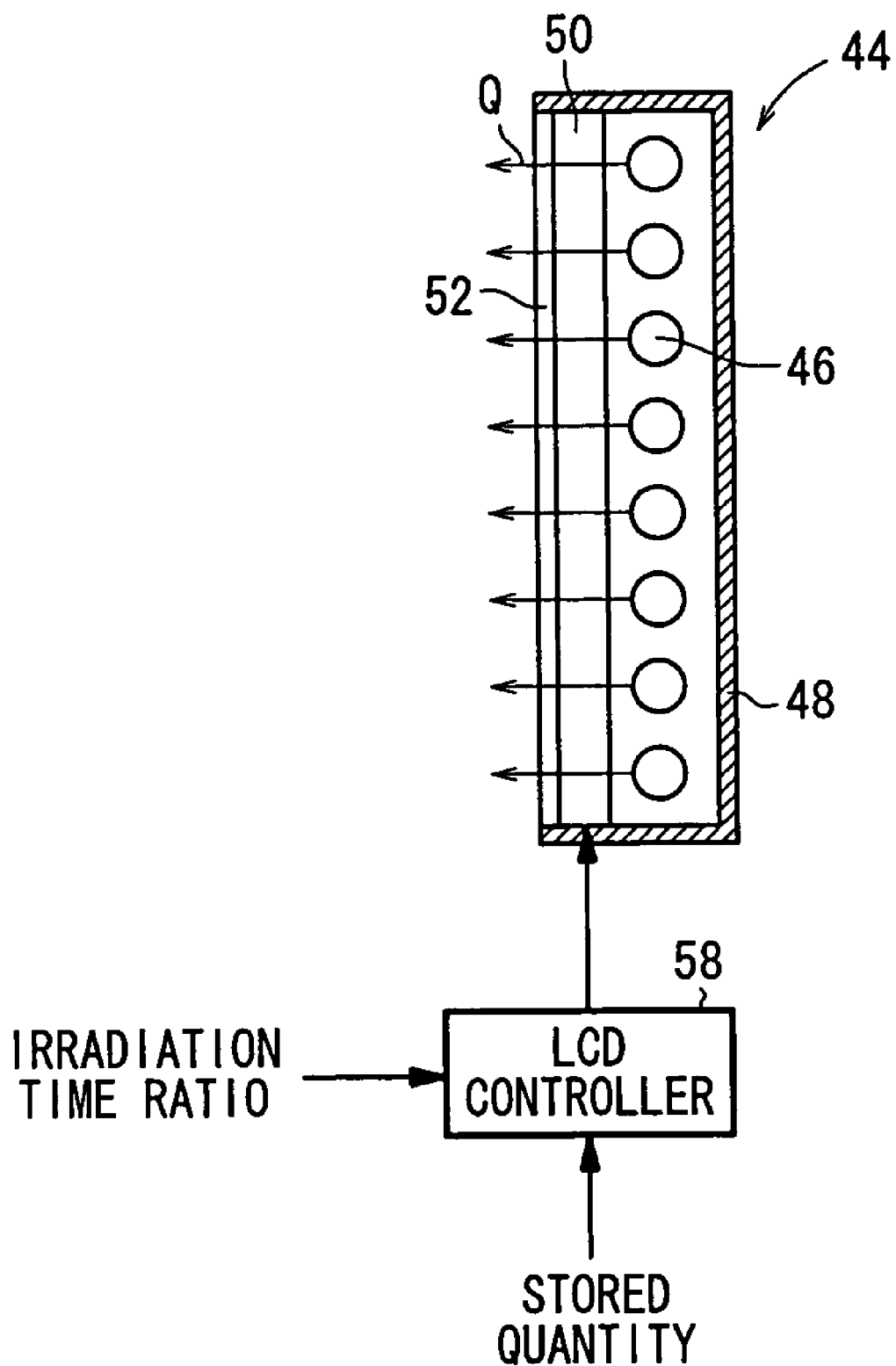
FIG. 7 is a vertical cross-sectional view of an erasing unit according to another embodiment of the present invention.

FIG. 7 shows in vertical cross section an erasing unit 44 according to another embodiment of the present invention. As shown in FIG. 7, the erasing unit 44 comprises a plurality of erasing light sources 46 housed in a casing 48 for emitting erasing light Q through an opening of the casing 48, and an LCD (Liquid Crystal Display) panel 50 and a filter 52 that are disposed in the opening of the casing 48. Each of the erasing light sources 46 comprises a xenon tube, a cold-cathode tube, or the like which is capable of emitting erasing light Q in a full wavelength range covering short to long wavelengths for erasing residual radiation energy. The LCD panel 50 and the filter 52 jointly make up a filtering means.

Figure 8:
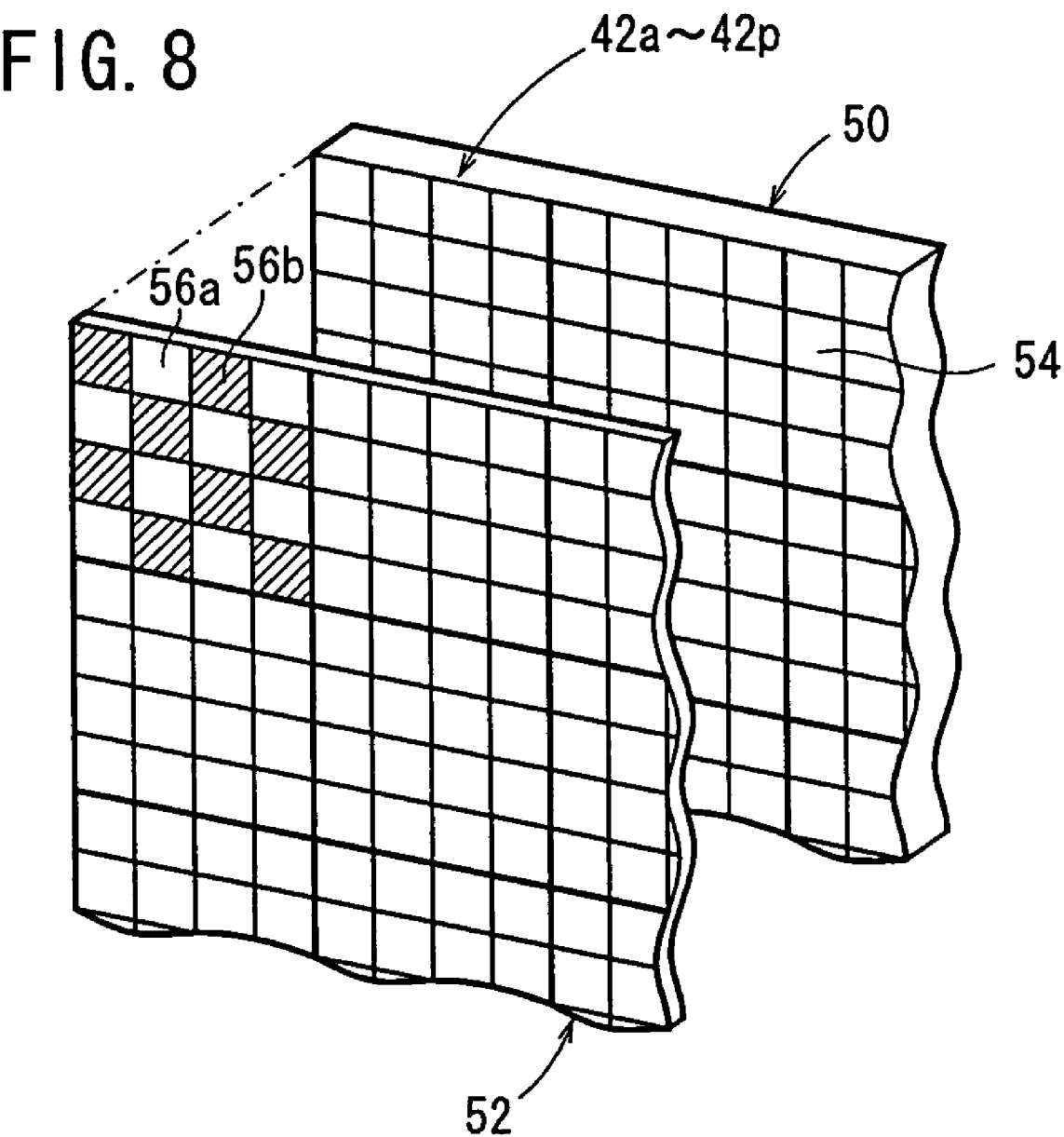
FIG. 8 is a fragmentary perspective view of a filtering means of the erasing unit shown in FIG. 7.

As shown in FIG. 8, the LCD panel comprises a matrix of LCD devices 54 (liquid crystal shutters). As with the erasing unit 22 according to the previous embodiment, the erasing unit 44 has its entire erasing light emitting area divided into a plurality of erasing blocks 42a through 42p corresponding respectively to the divided areas of the stimulable phosphor panel IP. The filter 52 comprises a number of filter elements 56a, 56b alternately arranged in a two-dimensional matrix in alignment with the respective LCD devices 54. The filter elements 56a serve to pass the erasing light Q (first erasing light) in the full wavelength range, and the filter elements 56b serve to pass the erasing light Q (second erasing light) in a wavelength range exclusive of the short wavelength range. The filter elements 56a may be dispensed with.

The erasing unit 44 operates as follows: Based on the maximum level of stored radiation energy with respect to each of the divided areas supplied from the stored quantity calculator 36, the erasing unit 44 calculates an amount of erasing energy that is required to erase residual radiation energy with each of the erasing blocks 42a through 42p. Then, an LCD controller 58 (see FIG. 7) controls the LCD devices 54 according to the calculated amount of erasing energy and the irradiation time ratio supplied from the irradiation time ratio setting unit 38. Specifically, the LCD controller 58 renders those LCD devices 54 corresponding to the filter elements 56a transmissive, applying the first erasing light Q1 including the radiation in the short wavelength range to the stimulable phosphor panel IP for a given time based on the irradiation time ratio. Thereafter, the LCD controller 58 renders those LCD devices 54 corresponding to the filter elements 56b transmissive, applying the second erasing light Q2 exclusive of the radiation in the short wavelength range to the stimulable phosphor panel IP for a given time based on the irradiation time ratio. As a result, the residual radiation image remaining in the stimulable phosphor panel IP can reliably be removed thoroughly from the stimulable phosphor panel IP.

Although certain preferred embodiments of the present invention have been shown and described in detail, it should be understood that various changes and modifications may be made therein without departing from the scope of the appended claims.

What is claimed is:

1. An apparatus for erasing a residual radiation image from a stimulable phosphor panel by applying erasing light to the stimulable phosphor panel after a radiation image has been read from the stimulable phosphor panel by applying stimulating light to the stimulable phosphor panel, comprising:
   stored quantity detecting means for dividing the stimulable phosphor panel into a plurality of areas, and detecting a quantity of radiation energy stored in each of said areas; and
   an erasing unit for applying the erasing light having a level of erasing energy depending on the detected quantity of radiation energy stored in each of said areas, to said stimulable phosphor panel with respect to each of the divided areas.

2. An apparatus according to claim 1, wherein said stored quantity detecting means calculates the quantity of radiation energy stored in each of said areas from said radiation image read from said stimulable phosphor panel.

3. An apparatus according to claim 1, wherein said stored quantity detecting means comprises a radiation dose detector for detecting a dose of radiation applied to each of said areas of said stimulable phosphor panel, and said stored quantity detecting means calculates the quantity of radiation energy stored in each of said areas from the detected dose of radiation.

4. An apparatus according to claim 1, wherein said erasing unit has a plurality of erasing blocks for applying said erasing light to said areas of said stimulable phosphor panel, and said erasing unit controls the erasing energy of said erasing light emitted from each of said erasing blocks according to said quantity of radiation energy stored in each of said areas.

5. An apparatus according to claim 4, wherein each of said erasing blocks comprises light-emitting elements for emitting said erasing light, and said erasing unit controls the erasing energy of said erasing light emitted from each of said light-emitting elements according to said quantity of radiation energy stored in each of said areas.

6. An apparatus according to claim 4, wherein each of said erasing blocks comprises filtering means for controlling the erasing energy of said erasing light, and said erasing unit applies said erasing light through said filtering means to said stimulable phosphor panel.

7. An apparatus according to claim 6, wherein said filtering means has a liquid crystal shutter for selectively transmitting and blocking said erasing light.

8. An apparatus according to claim 4, wherein each of said erasing blocks comprises:
   first erasing elements for emitting first erasing light including a radiation in a short wavelength range; and
   second erasing elements for emitting second erasing light including only a radiation in a long wavelength range;
   wherein said first erasing light is applied to said stimulable phosphor panel, and thereafter said second erasing light is applied to said stimulable phosphor panel.

9. An apparatus according to claim 8, wherein an irradiation time ratio for said first erasing light and said second erasing light to be applied to said stimulable phosphor panel is controlled according to said quantity of radiation energy stored in each of said areas.

10. An apparatus according to claim 9, further comprising:
    irradiation time ratio storing means for storing said irradiation time ratio for said first erasing light and said second erasing light with respect to said quantity of radiation energy stored in each of said areas.

11. An apparatus according to claim 1, wherein the erasing unit applies an erasing light having a level of erasing energy for each area of said areas depending on the detected quantity of radiation stored in the particular area.

12. An apparatus according to claim 1, wherein the erasing unit applies at least two different levels of erasing energy to two different respective plurality of areas depending on the detected quantity of radiation energy in each of said areas.

13. An apparatus according to claim 1, wherein said level of erasing energy of the erasing light is a measurement of the energy of the constituent particles of the erasing light.

14. An apparatus according to claim 1, wherein said level of erasing energy of the erasing light is a measurement of the ratio of the wavelengths of the erasing light applied.

15. An apparatus according to claim 1, wherein said level of erasing energy of the erasing light is a measurement of the energy of the constituent particles of the erasing light per unit of time.

16. A method of erasing a residual radiation image from a stimulable phosphor panel by applying erasing light to the stimulable phosphor panel after a radiation image has been read from the stimulable phosphor panel by applying stimulating light to the stimulable phosphor panel, comprising the steps of:
   detecting a quantity of radiation energy stored in said stimulable phosphor panel with respect to each of divided areas of the stimulable phosphor panel; and
   applying the erasing light having a level of erasing energy depending on the detected quantity of radiation energy stored in each of said areas, to said stimulable phosphor panel with respect to each of the divided areas.

17. A method according to claim 16, wherein said step of applying the erasing light comprises the steps of:
   applying first erasing light including a radiation in a short wavelength range to said stimulable phosphor panel; and
   thereafter, applying second erasing light including only a radiation in a long wavelength range to said stimulable phosphor panel.

18. A method according to claim 17, further comprising the step of:
   controlling an irradiation time ratio for said first erasing light and said second erasing light to be applied to said stimulable phosphor panel according to said quantity of radiation energy stored in each of said areas.

19. A method according to claim 17, further comprising the step of:
   controlling an irradiation time ratio for said first erasing light and said second erasing light to be applied to each area of said areas of the stimulable phosphor panel according to said quantity of radiation energy stored in the particular area.

20. A method according to claim 16, wherein the step of applying the erasing light further comprises:
   applying a erasing light to each area of said areas having a level of erasing energy depending on the detected quantity of radiation stored in the particular area.

21. A method according to claim 16, wherein said level of erasing energy of the erasing light is a measurement of the energy of the constituent particles of the erasing light.

22. A method according to claim 16, wherein said level of erasing energy of the erasing light is a measurement of the ratio of the wavelengths of the erasing light applied.

23. A method according to claim 16, wherein said level of erasing energy of the erasing light is a measurement of the energy of the constituent particles of the erasing light per unit of time.

* * * * *